(12) United States Patent
Spero et al.

(10) Patent No.: US 6,921,381 B2
(45) Date of Patent: Jul. 26, 2005

(54) LAPAROSCOPIC SPRAY DEVICE AND METHOD OF USE

(75) Inventors: Richard Spero, Brentwood, CA (US); Atif Yardimci, Northbrook, IL (US); Gordon Epstein, Fremont, CA (US)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 0 days.

(21) Appl. No.: 09/972,495

(22) Filed: Oct. 5, 2001

(65) Prior Publication Data

US 2003/0069537 A1 Apr. 10, 2003

(51) Int. Cl.⁷ .............................................. A61M 37/00
(52) U.S. Cl. ........................................................ 604/82
(58) Field of Search ............................ 604/82–92, 264, 604/191, 187; 222/137

(56) References Cited

U.S. PATENT DOCUMENTS

| | | |
|---|---|---|
| 4,978,336 A | 12/1990 | Capozzi et al. |
| 4,979,942 A | 12/1990 | Wolf et al. |
| 5,033,650 A | 7/1991 | Colin et al. |
| 5,104,375 A | 4/1992 | Wolf et al. |
| 5,116,315 A * | 5/1992 | Capozzi et al. ............... 604/82 |
| 5,147,323 A | 9/1992 | Haber et al. |
| 5,167,623 A | 12/1992 | Cianci et al. |
| 5,199,949 A | 4/1993 | Haber et al. |
| 5,240,146 A | 8/1993 | Smedley et al. |
| 5,253,785 A | 10/1993 | Haber et al. |
| 5,271,527 A | 12/1993 | Haber et al. |
| 5,423,752 A | 6/1995 | Haber et al. |
| 5,437,650 A | 8/1995 | Larkin et al. |
| 5,443,183 A | 8/1995 | Jacobsen et al. |
| 5,474,540 A * | 12/1995 | Miller et al. ................. 604/191 |
| 5,478,323 A * | 12/1995 | Westwood et al. .......... 604/191 |
| 5,582,596 A * | 12/1996 | Fukunaga et al. ........... 604/191 |
| 5,605,255 A * | 2/1997 | Reidel et al. ................ 222/137 |
| 5,637,101 A | 6/1997 | Shillington |
| 5,814,022 A | 9/1998 | Antanavich et al. |
| 5,918,772 A | 7/1999 | Keller et al. |
| 5,984,373 A | 11/1999 | Fitoussi et al. |
| 6,047,861 A * | 4/2000 | Vidal et al. .................. 222/137 |
| 6,059,749 A | 5/2000 | Marx |
| 6,063,055 A | 5/2000 | Epstein et al. |
| 6,065,645 A | 5/2000 | Sawhney et al. |
| 6,096,011 A | 8/2000 | Trombley, III et al. |
| 6,099,511 A | 8/2000 | Devos et al. |
| 6,132,396 A | 10/2000 | Antanavich et al. |
| 6,146,354 A | 11/2000 | Beil |
| 6,186,363 B1 | 2/2001 | Keller et al. |
| 6,234,994 B1 | 5/2001 | Zinger |

FOREIGN PATENT DOCUMENTS

| | | |
|---|---|---|
| EP | 0 424 068 A2 | 4/1991 |
| EP | 0 634 140 A1 | 1/1995 |
| WO | WO 95/06495 | 3/1995 |
| WO | WO 96/39212 | 12/1996 |
| WO | WO 97/28834 | 8/1997 |
| WO | WO 98/10704 | 3/1998 |
| WO | WO 00/18469 | 4/2000 |
| WO | WO 01/24869 A1 | 4/2001 |

* cited by examiner

Primary Examiner—Nicholas D. Lucchesi
Assistant Examiner—Matthew F DeSanto
(74) Attorney, Agent, or Firm—Jeffrey Nichols

(57) ABSTRACT

A laparoscopic spray device for selectively applying a multiple component material dispensed from a multiple component material applicator to a surgical site in vivo is disclosed. The device comprises an interface member capable of engaging a multiple component applicator, a body having at least two lumens therein, and a detachable spray tip in fluid communication with the body. The detachable spray tip includes a mixing chamber having at least one flexible mixing member positioned therein which is capable of creating a turbulent flow within a mixing chamber. In addition, the at least one mixing member prevents a back flow of material from the mixing chamber to the at least two lumens. The present invention is particularly useful in remotely applying multiple component tissue adhesives to an internal incision.

23 Claims, 10 Drawing Sheets

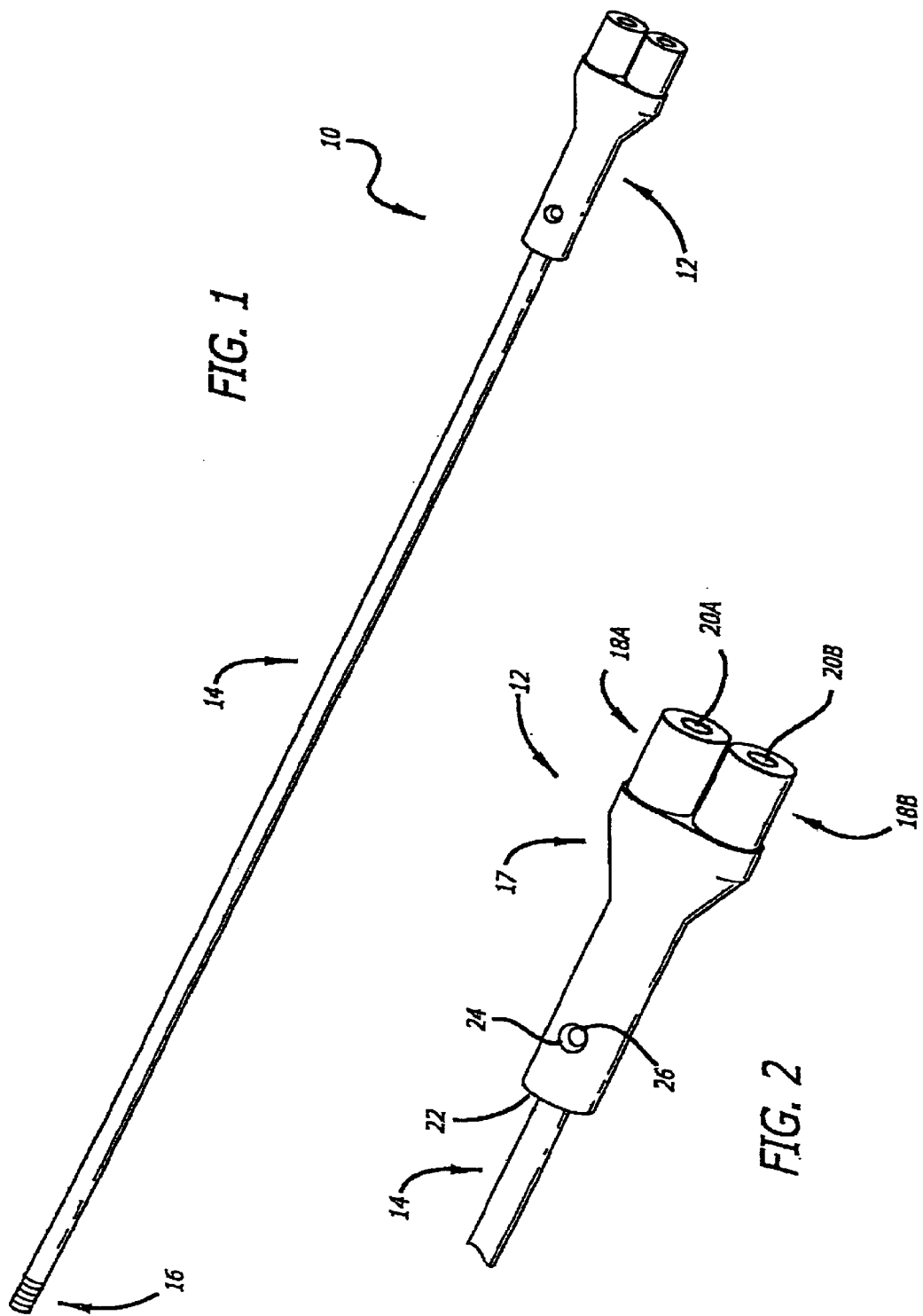

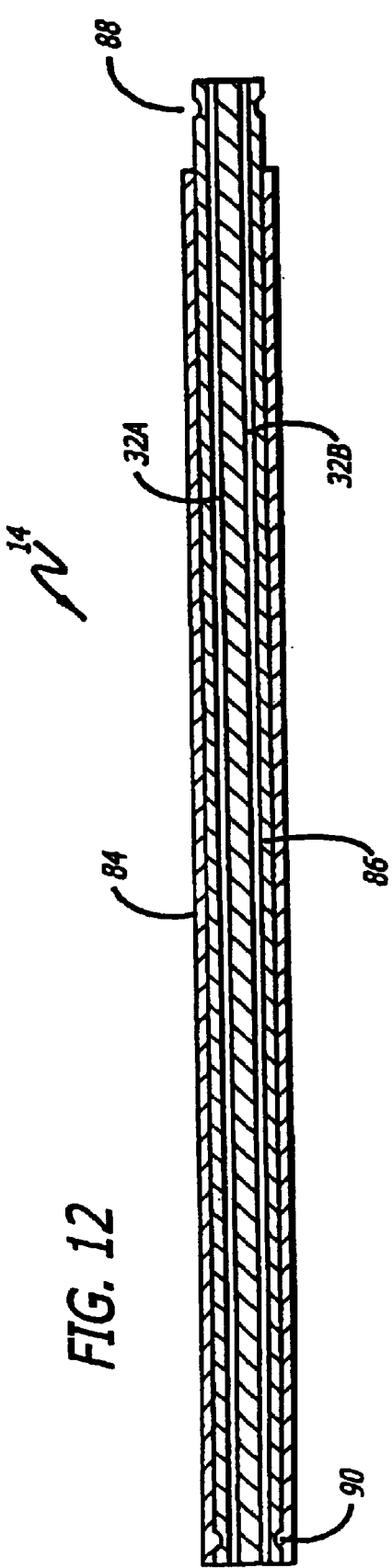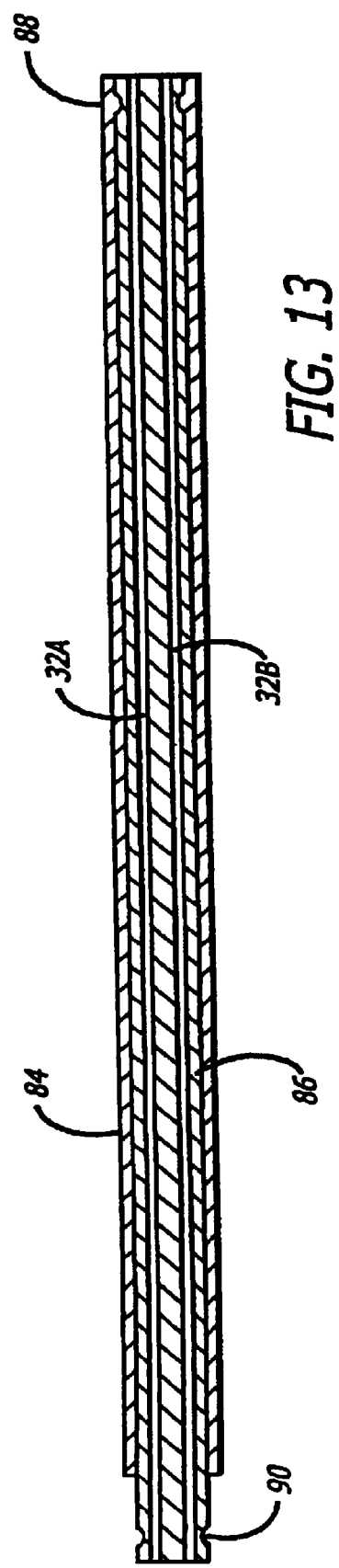

LAPAROSCOPIC SPRAY DEVICE AND METHOD OF USE

BACKGROUND OF THE INVENTION

In recent years, minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

One example of a common minimally invasive surgery involves laparoscopic surgical procedures. Laparoscopic procedures may be used to treat hernias, colon dysfunctions, gastroesophageal reflux disease, and gallbladder disorders. Typically, the patient undergoing the procedures will return home hours after undergoing surgery.

Generally, laparoscopic procedures require making at least one small incision in the patient's abdomen near the area of interest. A cannula or trocar may be inserted into to the incision to limit blood loss and reduce the likelihood of infection. Thereafter, various surgical instruments are introduced into the patient's body through the incision. Generally, these instruments enable the surgeon to visualize the inside of the patient's body and access the internal organs of the patient. Current laparoscopic surgical instruments include cameras, scissors, dissectors, graspers and retractors. Generally, these instruments include a handle attached to an elongated body having a distal tip used to execute the particular procedure. The handle, which remains outside the patient's body, is used by the surgeon to control the operation of the instrument during the procedure.

One challenge presented when performing minimally invasive surgical procedures relates to closing an incision made within the patient's body by a cutting laparoscopic instrument. As opposed to conventional surgical procedures, the surgeon's access to the site of the incision is greatly reduced during minimally invasive procedures. As a result, several knot pushing devices capable of advancing suture knots formed outside the patient's body to an area of interest in vivo have been developed. Typically, a suturing laparoscopy device is inserted into the patient's body and advanced to the incised area. A needle is advanced through the various tissue portions proximate the incision, thereby securing the suture material to the tissue. Thereafter, the suturing device is removed from the patient's abdomen leaving the suture material attached to the tissue. A knot is formed in the suture material and advanced along the suture material by the knot pusher to the incision, thereby applying the suture knot. The extraneous suture material is trimmed with laparoscopic scissors once the incision is adequately sutured. Occasionally, the suture knot becomes entangled in the suture material during the advancement process. The surgeon is then required to remove the entangled suture material from the incision area and reattach new suture material, thereby increasing the likelihood of infection and the patient's exposure to anesthesia.

Recently, the use of tissue sealants and other biological adhesive materials has emerged as an alternate technique of closing incisions. Preferred tissue sealants include fibrin, which is comprised of thrombin and a fibrinogen material, although other multiple component materials are available. Typically, the individual components of the adhesive material are stored in isolated reservoirs. When mixed, these components may coagulate very quickly, yielding an adhesive gel within perhaps 10 or 20 seconds. When applied to the exterior of the body, or when considerable access to the application site is possible, the rapid coagulative properties of the tissue sealant are welcomed. Though desirable for use during minimally invasive procedures, such fast-acting properties of conventional tissue sealants and adhesive have presented potential problems of fouling or clogging during the application of tissue sealants through laparoscopic devices, which typically results in the destruction of the device.

Thus, there is a need for a device capable of effectively delivering a multiple component tissue sealant to a location in vivo through from a remote location.

BRIEF SUMMARY OF THE INVENTION

The present invention solves the problem of effectively delivering multiple sealant components through a laraoscopic device to a location in vivo. Those skilled in the art will appreciate that the present invention enables a user to apply a multiple component material to an incision site within the patient's body from a remote location without the fouling or clogging problems associated with prior art devices.

In one aspect, the present invention provides a laparoscopic spray device comprising an interface member capable of detachably coupling to a multiple component material applicator, an elongated body having at least two lumens formed therein in fluid communication with the interface member, and a detachable spray tip having a mixing chamber therein coupled to the elongated body useful in generating a spray to apply the material in vivo. The at least one flexible mixing member of the present invention is capable of generating a turbulent flow within the mixing chamber, thereby resulting in impingement mixing of the components of the multiple component material. In addition, the at least one flexible mixing member may be used to prevent a back flow of material from the mixing chamber to the at least two lumens within the elongated body. Those skilled in the art will appreciate that a material applicator may be coupled to the present invention in a plurality of ways, including, without limitation, in slip-fit relation, in luer-lock relation, and in screw-like relation.

In another embodiment of the present invention, the laparoscopic spray device comprises an interface member capable of detachably coupling to a material applicator, an elongated body having at least two lumens therein in fluid communication with the at least two transport lumens within the interface member, and a spray tip having a mixing chamber containing at least one mixing member therein detachably coupled to and in fluid communication with the elongated body. The interface member further comprises at least two coupling members having at least two receiving apertures formed therein. The receiving apertures are capable of coupling to the material applicator and are in fluid communication with at least two transport lumen positioned within the interface member. The elongated body comprises a stationary inner body member positioned within a longitudinally slide-able outer body member. The stationary inner body includes a spray tip receiver adapted to receive a detachable spray tip. The slide-able outer body is capable of being advanced and retracted to cover and expose, respectively, the spray tip receiver. The at least one flexible mixing member of the present invention is capable of generating turbulent flow within the mixing chamber, thereby resulting in impingement mixing of the components of the multiple component material. In addition, the at least one flexible mixing member may be used to prevent a back flow of material from the mixing chamber to the at least two lumens within the elongated body.

The present invention also provides a method of mixing a multiple component material with at least one flexible mixing member. To practice the present invention the user positions at least one flexible mixing member proximate to the entrance of a material mixing chamber. The mixing chamber is attached to at least two component lumens which are in fluid communication with a multiple component source. The individual components are advanced through the separate lumens towards the mixing chamber. Thereafter, the at least one flexible mixing member engages the individual components and forces the components together, thereby generating turbulent flow within the mixing chamber. The generation of turbulent flow within the mixing chamber results in impingement mixing of the components which yields a mixed material. In addition to enhancing the impingement mixing effects, the at least one flexible mixing member prevents the back flow of material from the mixing chamber to the at least two component lumens. Thereafter, the mixed material is advanced through an aperture formed in the mixing chamber and applied to a work surface.

Other objects, features, and advantages of the present invention will become apparent from a consideration of the following detailed description.

BRIEF DESCRIPTION OF THE DRAWINGS

The apparatus of the present invention will be explained in more detail by way of the accompanying drawings, wherein:

FIG. 1 shows a perspective view of the laparoscopic spray device of the present invention;

FIG. 2 shows a perspective view of the interface member the present invention;

FIG. 12 is a cross-section view of the elongated body of the present invention wherein the slidable outer sleeve is positioned over the spray tip receivers;

FIG. 13 is a cross-section view of the elongated body of the present invention wherein the slidable outer sleeve is positioned over the attachment channel;

DETAILED DESCRIPTION OF THE INVENTION

Figure 3:
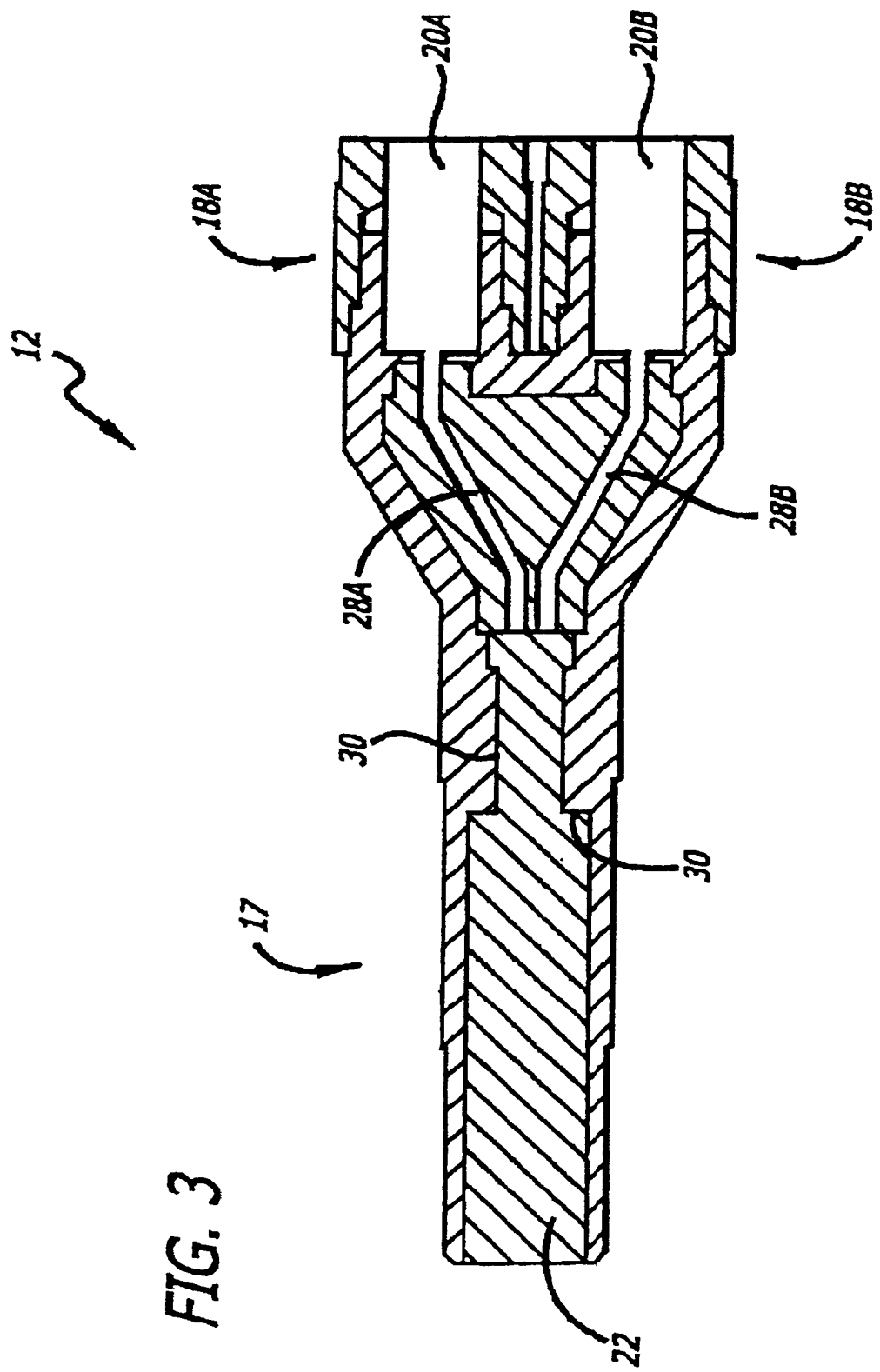
FIG. 3 shows a cross-sectional view of the interface member the present invention.

Disclosed herein is a detailed description of various illustrated embodiments of the present invention. This description is not to be taken in a limiting sense, but is made merely for the purpose of illustrating the general principles of the invention. The section titles and overall organization of the present detailed description are for the purpose of convenience only and are not intended to limit the present invention.

The laparoscopic spray device of the present invention is used in conjunction with a multiple component applicator to dispense a multiple component fluid to a work surface located within the body of a patient. Those skilled in the art will appreciate that the present invention is particularly well suited to dispense a multiple component tissue sealant, such as Fibrin, which is capable of effecting hemostasis or achieving other therapeutic results.

The laparoscopic spray device of the present invention is designed to permit the remote application of a multiple component fluid. Those skilled in the art will appreciate that the present invention may be adapted to functionally couple to a plurality of applicators, including, for example, multiple reservoir syringe-type applicators such as the DUPLOJECT™ syringe-type applicator manufactured by the Baxter Healthcare Corporation. It is anticipated as being within the scope of the present invention to produce a laparoscopic spray device capable of functionally coupling with a plurality of applicators in a plurality of sizes.

FIG. 1 shows a perspective view of the present invention. As shown, the laparoscopic spray device 10 comprises an interface member 12 in fluid communication with an elongated body 14 having a spray head 15 attached thereto. Those skilled in the art will appreciate that the present invention may be manufactured from a plurality of materials, including, without limitation, polyethylene, polypropylene, polystyrene, or a like material. A plurality of materials having different physical properties may be used to manufacture various portions of the present invention. For example, the interface member 12 and elongated body 14 may be made rigid, while the spray tip 15 is resilient. In an alternate embodiment, the interface member 12 may be manufactured from a rigid material while the elongated body 14 and spray tip 15 is resilient.

FIG. 2 shows a perspective view of the interface member 12 of the present invention. The interface member 12 comprises a member body 17 in communication with at least two coupling members 18A, 18B. A first receiving aperture 20A is formed within the first coupling member 18A. Similarly, a second receiving aperture 20B is formed within the second coupling member 18B. The receiving apertures 20A, 20B are sized to receive a material applicator (not shown). Those skilled in the art will appreciate that the interface member 12 may be manufactured in a plurality of sizes to receiving a plurality of material applicators. The interface member 12 further includes an elongated body receiver 22 which is in communication with an attachment device aperture 24 sized to receive an attachment device 26 therein. The attachment device 26 removably couples the interface member 12 to the elongated body 14. Those skilled in the art will appreciate that the exemplary attachment devices 26 may include, without limitation, screws and buttons.

Figure 4:
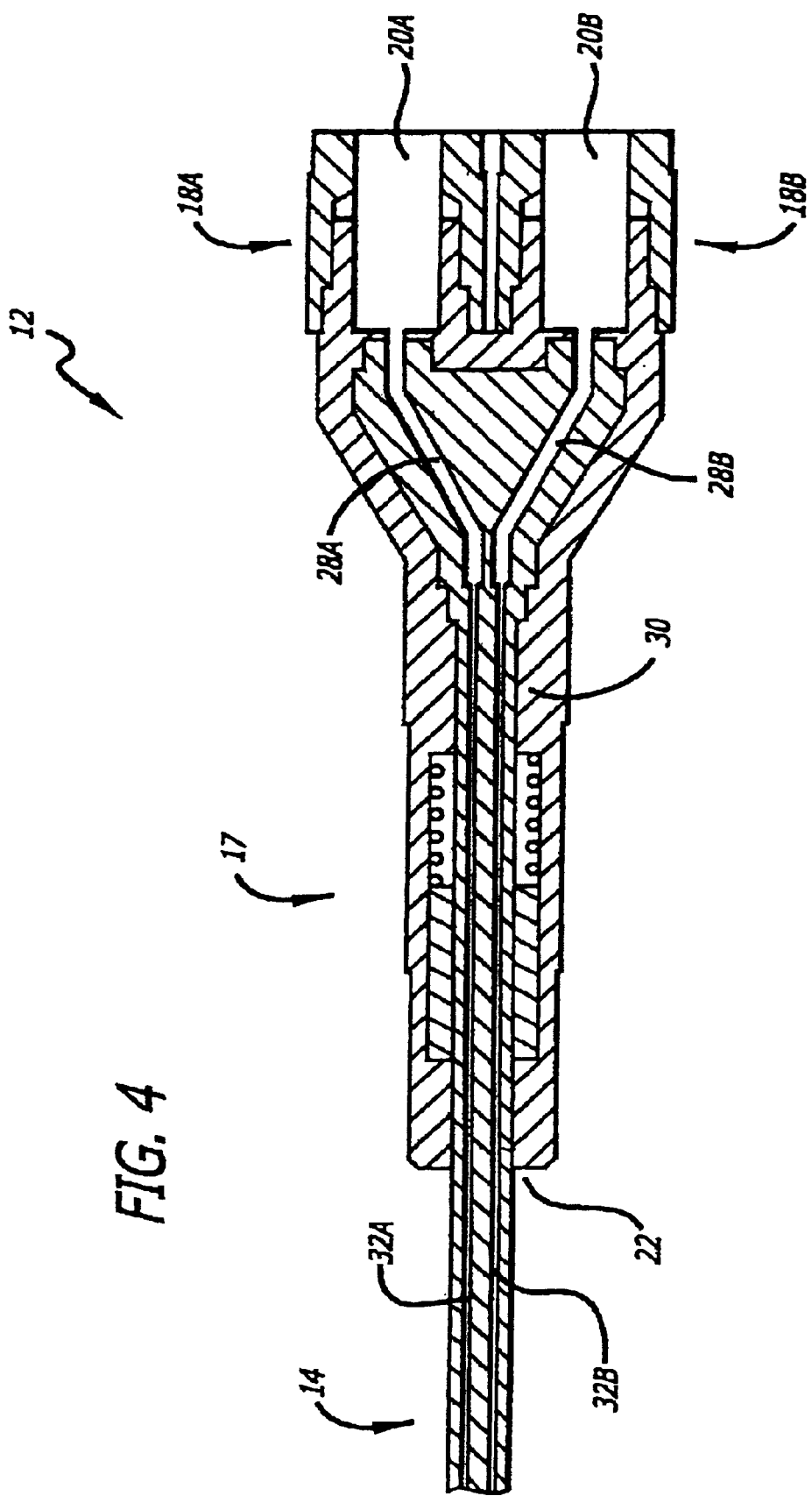
FIG. 4 shows a cross-sectional view of the interface member attached to the elongated body the present invention.

FIGS. 3–4 show several cross sectional views of the interface member 12 of the present invention. The receiving apertures 20A, 20B located within the coupling members 18A, 18B are in fluid communication with at least two transport lumens 28A, 28B located within the member body 17. As shown, the transport lumens 28A, 28B have a uniform diameter. In an alternate embodiment the transport lumens 28A, 28B may have different diameters. The transport lumens 28A, 28B terminate within the elongated body receiver 22. As shown in FIGS. 3 and 4, the elongated body receiver 22 includes at least one aligning member 30 therein. The aligning member 30 ensures that the at least two lumens 32A, 32B formed in the elongated body 14 are aligned with and are in fluid communication with the transport lumens 28A, 28B within the interface member 12. In addition, the aligning member 30 may apply a constrictive force to the elongated body 14, thereby assisting in the retention thereof.

Figure 5:
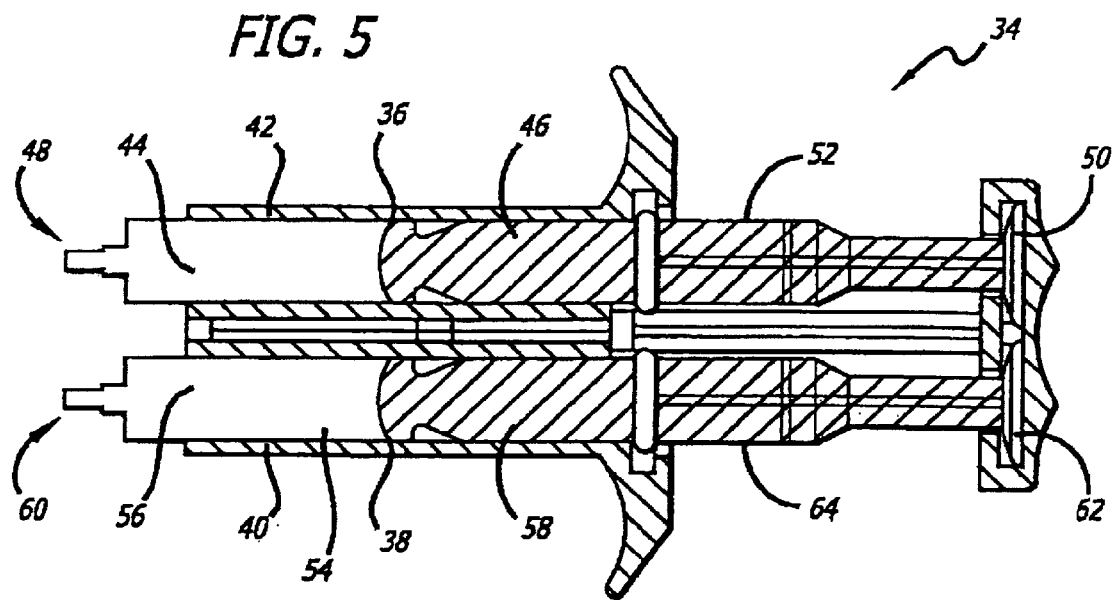
FIG. 5 shows a cross-sectional view of a multiple syringe material applicator useful in applying a multiple component material to a work surface.

FIG. 5 shows a cross-sectional view of an exemplary material applicator 34 capable of coupling to the present invention. As shown, the material applicator 34 comprises at least a first syringe device 36 and a second syringe device 38 coupled by a syringe coupler 40. It should be understood that the material applicator 34 of the present invention may comprise a plurality of material reservoirs, and the present embodiment should not be construed as limiting.

The first syringe device 36 comprises a first syringe reservoir 42 storing a first component 44 and a first syringe piston 46, positionable within the first syringe reservoir 42. The first syringe device 36 has a first syringe dispensing tip 48 connected to the first syringe reservoir 42 extending beyond the syringe coupler 40 and a first syringe pusher 50, which is attached to the first piston rod 52.

Likewise, second syringe device 38 comprises a second syringe reservoir 54 storing a second component 56 and a second syringe piston 58, positionable within the second syringe reservoir 54. The second syringe device 38 has a second syringe dispensing tip 60 connected to the second syringe reservoir 54 extending beyond the syringe coupler 40, and a second syringe pusher 62, which is attached to the second piston rod 64.

Figure 6:
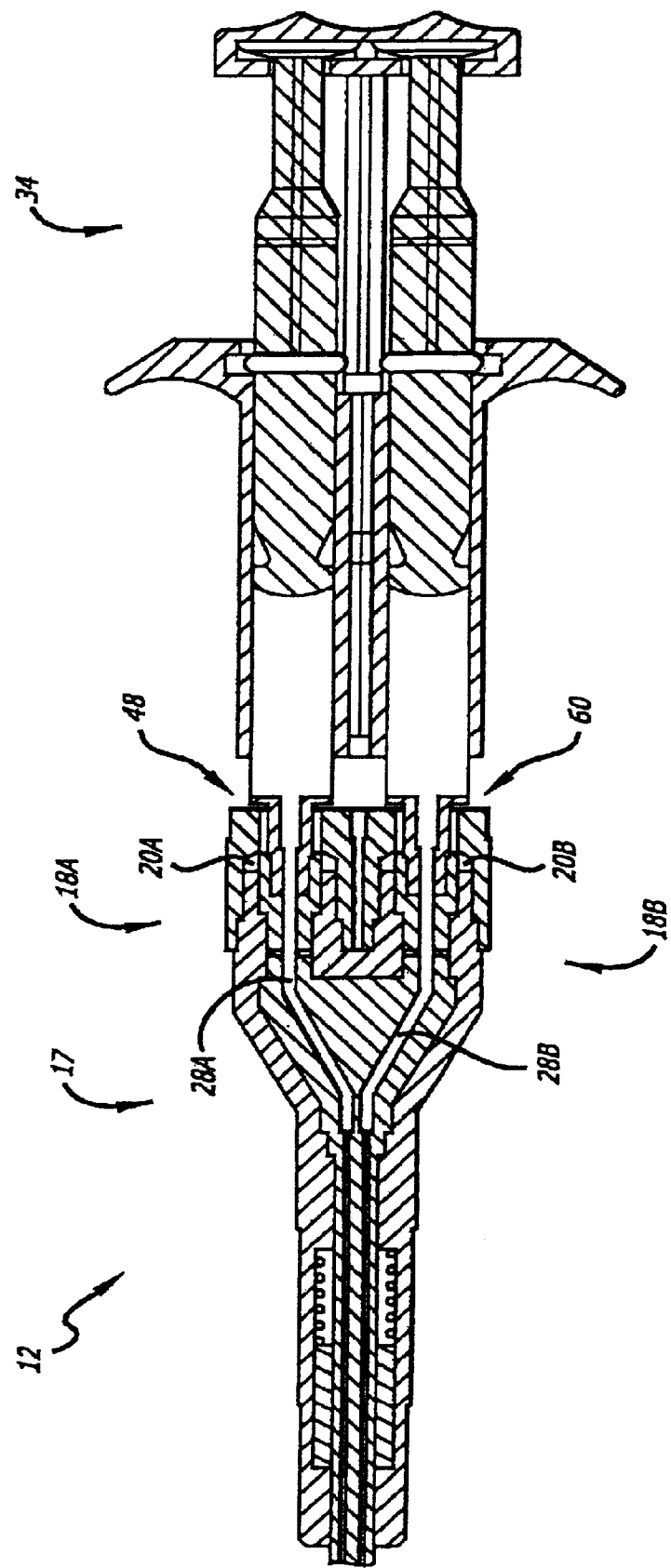
FIG. 6 shows a cross-sectional view of a multiple syringe material applicator coupled to the interface member of the present invention.

The coupling members 18A, 18B of the present invention may couple to the material applicator 34 in a plurality of ways, including, in screw-able relation or snap-fit relation. FIG. 6 shows one embodiment of the interface member 12 of the present invention coupled to a material applicator 34. As shown, the syringe dispensing tips 48, 60 are slidably positioned within the coupling members 18A, 18B, in a luer-lock relation. In one embodiment the coupling members 18A, 18B are manufactured from a resilient material such as a biologically compatible elastomer, thereby permitting the coupling members 18A, 18B to resiliently receive the dispensing tips 48, 60. Those skilled in the art will appreciate that the receiving apertures 20A, 20B formed in the coupling members 18A, 18B may be tapered to ensure that a sealable interface between the interface member 12 and the applicator 34 is obtained. In an alternate embodiment, the receiving apertures 20A, 20B is not tapered.

Figure 7:
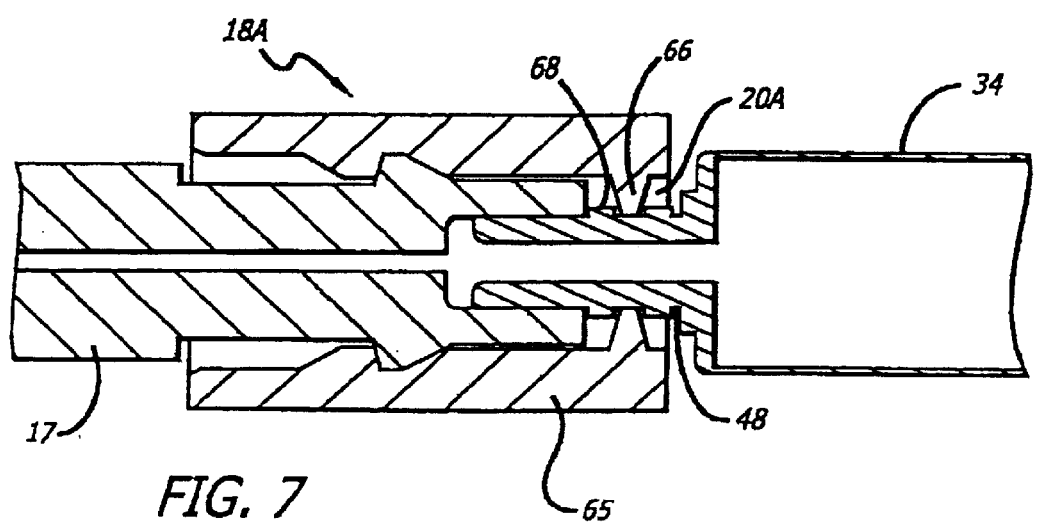
FIG. 7 shows a expanded cross-sectional view of an embodiment of the interface member of the present invention engaging a dispensing tip of a multiple syringe material applicator.

An alternate embodiment of the coupling members 18A, 18B is shown in FIG. 7. A coupling member 18A is shown, which comprises a rotate-able threaded sleeve 65 and includes a lock member 66 positioned within the receiving aperture 20A. The lock member 66 engages a tip thread 68 located on the dispensing tip 48 in a screw-like relation.

Figure 8:
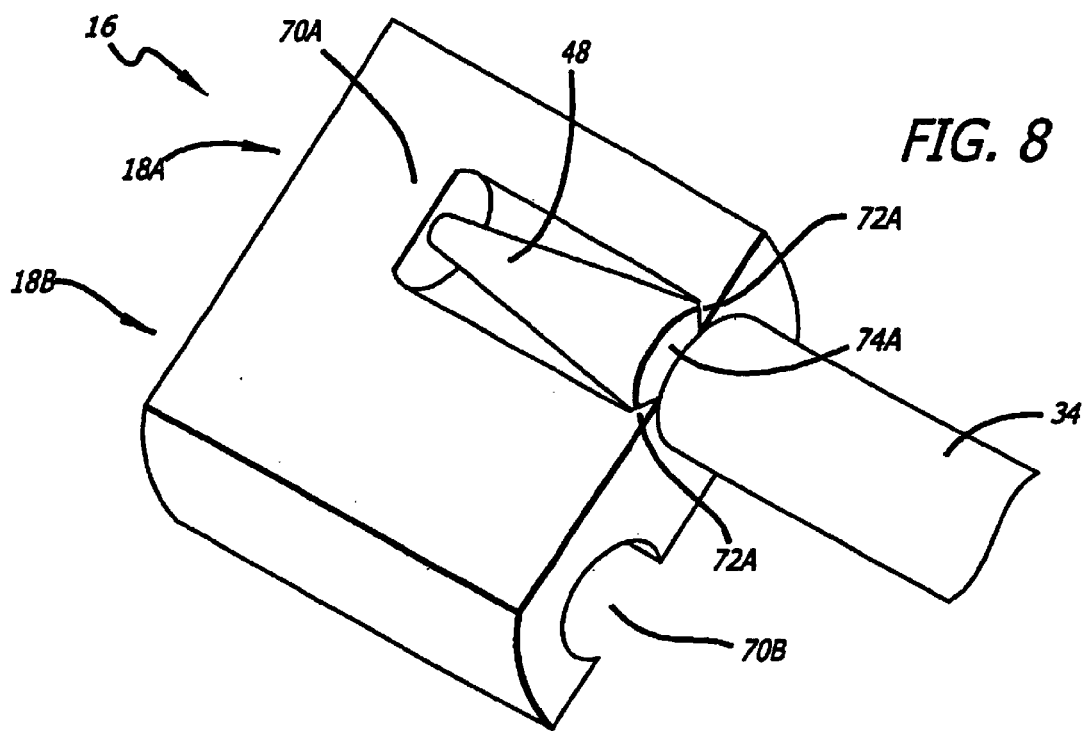
FIG. 8 shows a perspective of another embodiment of the interface member of the present invention engaging a dispensing tip of a multiple syringe material applicator.
Figure 9:
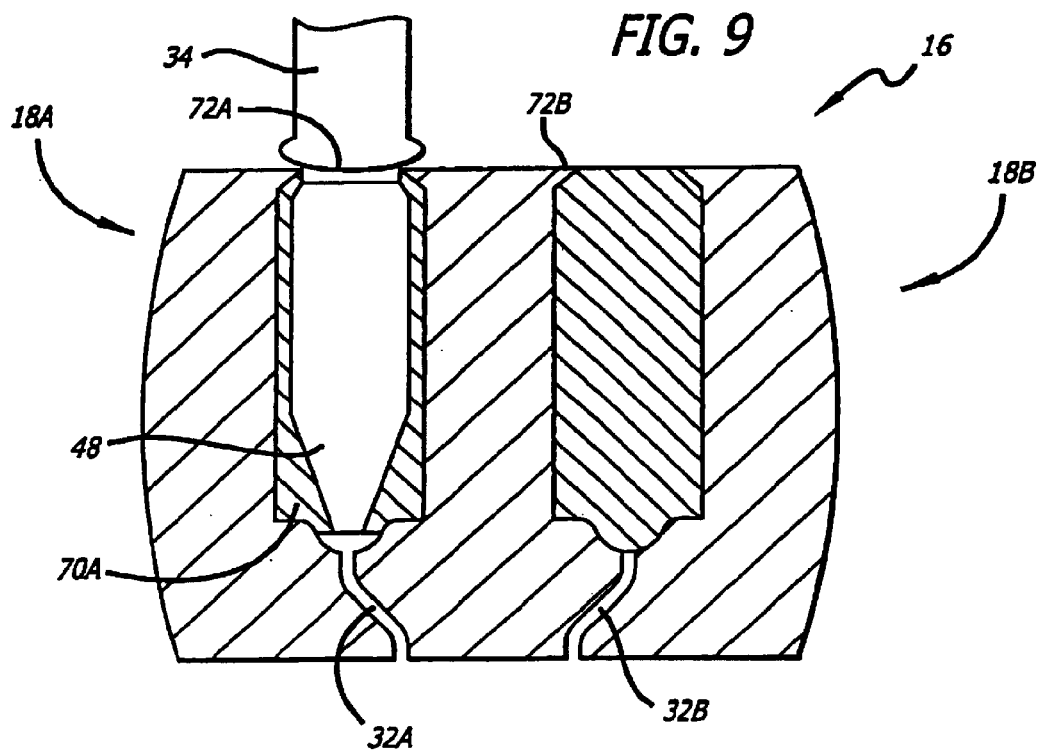
FIG. 9 shows a cross-sectional view of the embodiment of FIG. 8 wherein the interface member of the present invention is engaging a dispensing tip of a multiple syringe material applicator.

FIGS. 8 and 9 show an alternate embodiment of the coupling members of the present invention. As shown, the coupling members 18A, 18B may comprise engaging channels 70A, 70B formed in the member body 17. The receiving channels 70A, 70B include at least one lock ridge 72A, 72B positioned within each receiving channel 70A, 70B. The lock ridge 72A, 72B slide-ably engages at least one engaging channel 74A, 74B formed on the dispensing tips 48, 60 of the material applicator 34.

Figure 10:
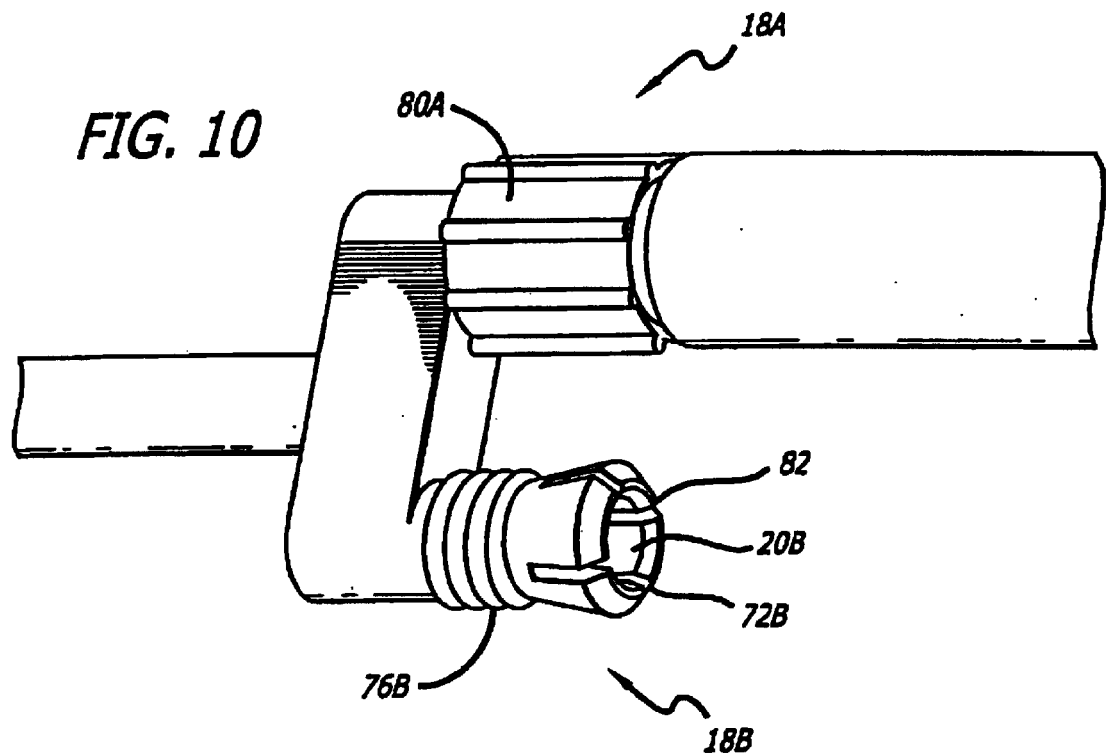
FIG. 10 shows a perspective of yet another embodiment of the interface member of the present invention engaging a dispensing tip of a multiple syringe material applicator.
Figure 11:
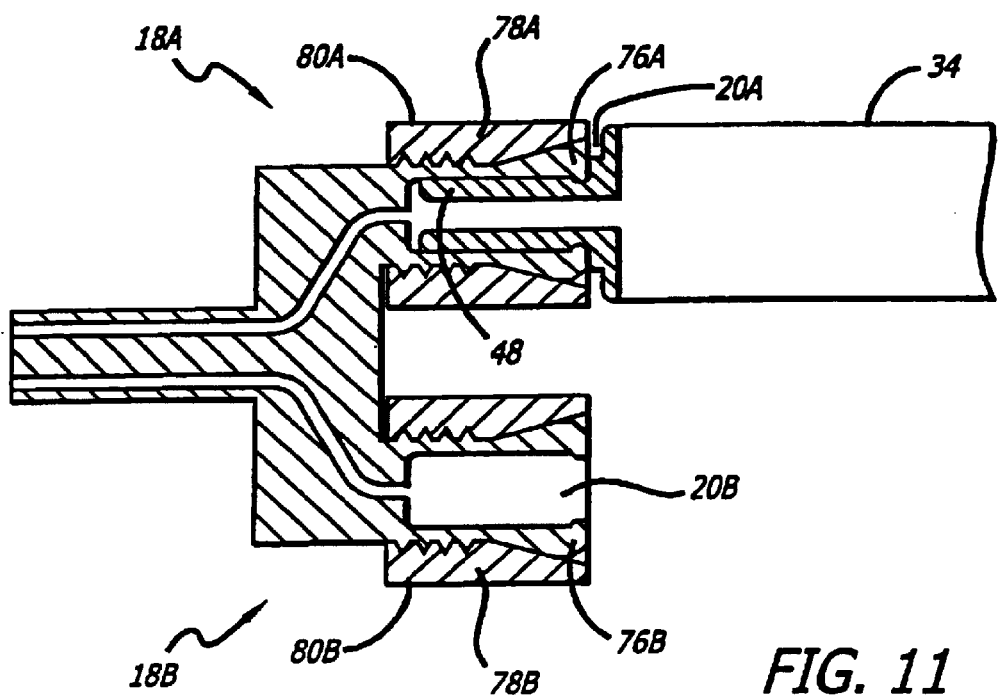
FIG. 11 shows a cross-sectional view of the embodiment of FIG. 10 wherein the interface member of the present invention is engaging a dispensing tip of a multiple syringe material applicator.

FIGS. 10 and 11 show yet another embodiment of the coupling members 18A, 18B of the present invention. As shown, the coupling members 18A, 18B each include a compressible collet 76A, 76B therein. Each collet 76A, 76B, which defines a receiving aperture 20A, 20B sized to be a slightly larger diameter than the inside diameter of the threaded outer sleeve 80A, 80B, includes a threaded base 78A, 78B. As shown, each collet 76A, 76B is tapered and includes a plurality of compression slits 82 positioned radially around the collet. During use each dispensing tip 48, 60 is inserted into the receiving aperture 20A, 20B defined by the individual collet 76A, 76B. Thereafter, the threaded outer sleeve 80A, 80B is positioned to engage the threaded base 78A, 78B and rotated. As a result, the threaded outer sleeve 80A, 80B forcibly compresses the collet 76A, 76B thereby decreasing the diameter of the receiving aperture 20A, 20B and applying a retentive force to the dispensing tips 48, 60 of the material applicator 34 positioned therein. Those skilled in the art will appreciate the dispensing tips 48, 60 of the material applicator 34 may, but need not, include a retaining channel (not shown) thereon.

FIG. 12 shows a cross-sectional view of the elongate body 14 of the present invention. As shown, the elongated body 14 includes a longitudinally slide-able outer sleeve 84 positioned around a stationary inner body 86. At least two elongated body lumens 32A, 32B are positioned within the inner body 86. The at least two elongated body lumens 32A, 32B are capable of engaging the transport lumens 28A, 28B positioned within the interface member 12. An attachment channel 88 is formed on the elongated body 14 thereby enabling the elongated body to engage attachment device 26 positioned on the interface member 12. The distal portion of the elongated body 14 includes a spray tip receiver 90 capable of receiving a detachable spray tip (not shown) thereon. As shown in FIG. 13, the outer sleeve 84 may be slidably retracted towards the attachment channel 88 thereby exposing the spray tip receiver 90.

Figure 14:
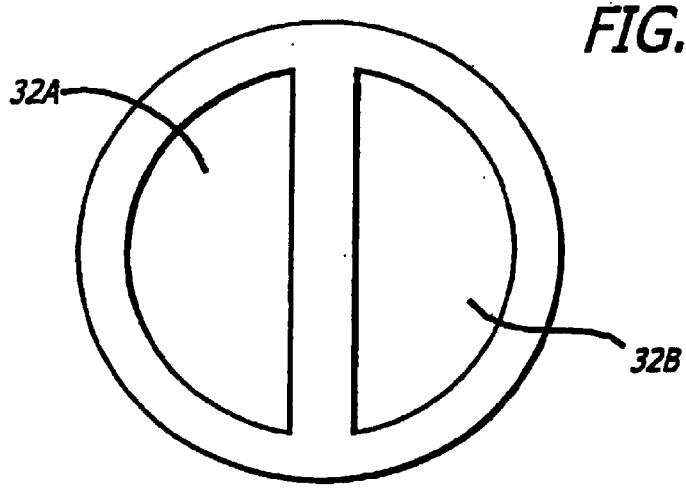
FIG. 14 is a cross-section view of the at least two lumens located within the elongated body of the present invention.

The elongated body lumens 32A, 32B positioned within the elongated body 14 may be formed in a plurality of shapes, including, without limitation, circular lumens and D-shaped lumens. FIG. 14 shows one embodiment wherein the elongated body lumens 32A, 32B are D-shaped. Those skilled in the art will appreciate that the D-shaped elongated body lumens 32A, 32B of the present embodiment allow a larger cross sectional area for the lumen in a smaller overall diameter shaft. As a result, less force is required to advance the individual components through the device with a flow rate sufficient to permit the sprayed application of the multiple component material.

Figure 15:
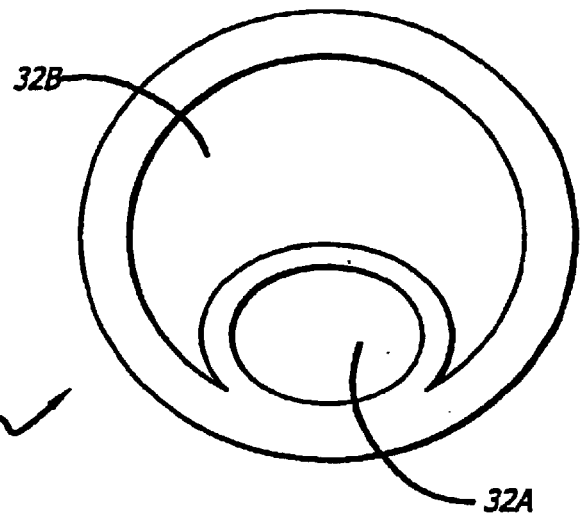
FIG. 15 is a cross-section view of an alternate embodiment of the at least two lumens located within the elongated body of the present invention.
Figure 16:
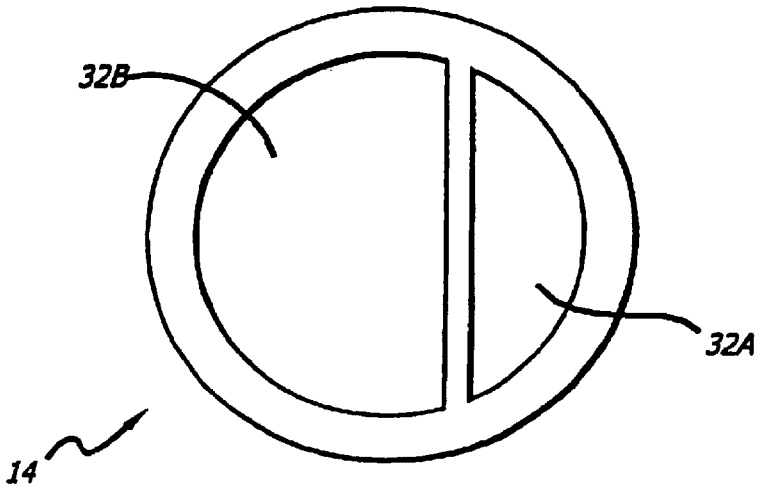
FIG. 16 is a cross-section view of another embodiment of the at least two lumens located within the elongated body of the present invention.

As shown in FIG. 14, the elongated body lumens 32A, 32B positioned within the elongated body 14 may have uniform diameters. Commonly, the individual components comprising the multiple component materials may have different viscosities and flow rates, or may require a disproportionate amount of one component in relation to another component. As such, in an alternate embodiment of the present invention the elongated lumens 32A, 32B may be different diameters to accommodate the different viscosities and flow rates of the component materials, or to account for the uneven distribution of one component in relation to another component. FIGS. 15 and 16 show cross-sectional views of alternate embodiments of the present invention wherein the elongated lumens 32A, 32B have different diameters to account for different viscosities and flow rate of individual components, or to dispense a disproportionate amount of one component in relation to another component. Similarly, the transport lumens 28A, 28B may also have different diameters or shapes as well. As shown in FIG. 15, the first elongated body lumen 32A has a diameter considerably smaller then the diameter of the second elongated body lumen 32B. Therefore, the device 10 will transport a greater volume of component material through the second elongated body lumen 32B with respect to the first elongated body lumen 32A. Similarly, FIG. 16 shows another embodiment of the present invention wherein the second elongated body lumen 32B is capable of transporting a larger volume of material therethrough with respect to the first elongated body lumen 32A.

Figure 17:
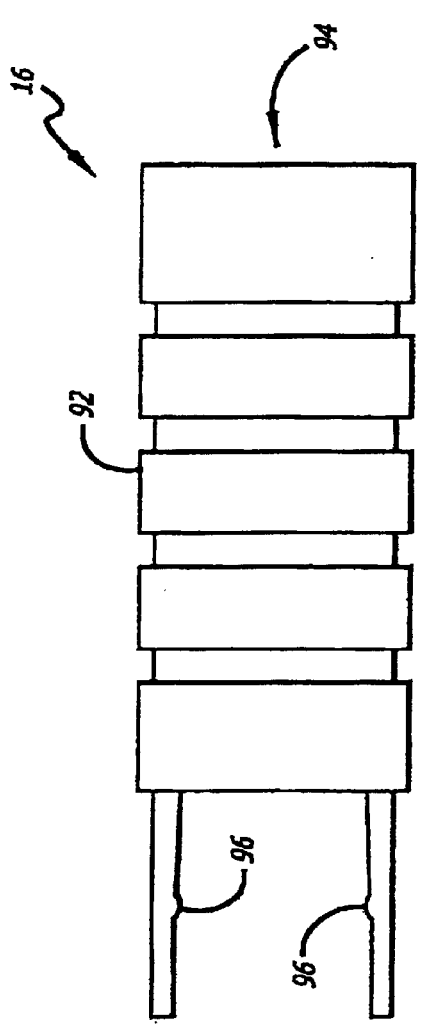
FIG. 17 is a side view of the detachable spray tip of the present invention.
Figure 18:
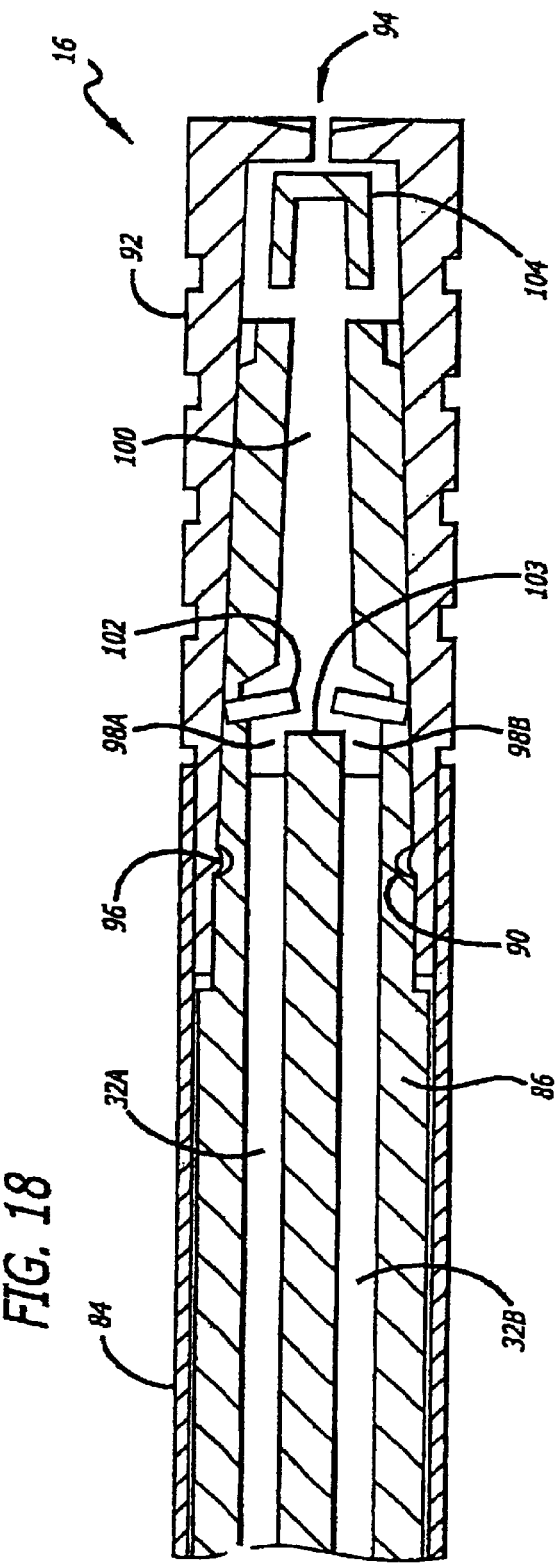
FIG. 18 is a cross-section view of the detachable spray tip of the present invention.

FIGS. 17 and 18 show various views of the detachable spray tip 15 of the present invention. As shown in FIG. 17, the exterior of the spray tip 15 includes a tip body 92 having a spray aperture 94 formed therein. The spray tip 15 further includes at least one low-profile mounting member 96 attached thereto, thereby enabling the spray tip 15 to detachably mount to the elongated body 14. Those skilled in the art will appreciate that the spray tip 15 may be manufactured from a plurality of materials, including, for example, biologically-compatible elastomers, plastics, and metals.

FIG. 18 shows a cross sectional view of the detachable spray tip 15 coupled to the elongated body 14 of the present invention. As shown, the at least one mounting member 96 is located between the outer body 84 and the stationary inner body 86 of the elongated body 14, and is engaging the spray tip receiver 90. Those skilled in the art will appreciate that the detachable spray tip 15 of the present invention may detachably couple to the elongated body 14 of the present invention in a plurality of ways, including, in snap-fit relation. At least two lumen receivers 98A, 98B receive the elongated body lumens 32A, 32B.

The spray tip 15 of the present invention further includes a mixing chamber 100 which is in communication with the at least two lumen receivers 98A, 98B. At least one flexible mixing member 102 is positioned within the mixing chamber 100, proximate to the at least two lumen receivers 98A, 98B. The at least one flexible mixing member 102 assists in causing impingement mixing of the at least two material components by forming a turbulent flow within the mixing chamber 100. During use, the individual components are advanced through the elongated body lumens 32A, 32B and individually engage the at least one mixing member 102 positioned within the mixing chamber 100. The force applied by the advancement of the individual components forces the at least one flexible mixing member 102 to flex in response thereto. The at least flexible mixing member 102 provides sufficient resistance to the applied force so as to form a narrowing element within the mixing chamber 100 and thereby force the individual components together within the mixing chamber 100. The resistance applied by the at least one flexible mixing member 102 in addition to the forward advancement of the material results in generation of turbulent flow within the mixing chamber 100. In addition to forming turbulent flow within the mixing chamber 100, the resilient nature of the at least one flexible mixing member 102 prevents a backflow of material from the mixing chamber 100 into the elongated body lumens 32A, 32B thereby acting as a directional flow valve. As shown in FIG. 18, the at least one mixing member 102 is capable of engaging the elongated body support member 103, thereby restricting access of the material to the elongated body lumens 31A, 32B from the mixing chamber 100 and preventing a backflow of material. The at least one flexible mixing member 102 may be manufactured in a plurality of shapes, including, for example, washer-like shapes.

A spray regulator 104 is positioned within the mixing chamber 100 proximate to the spray aperture 94. The spray regulator 104 further ensures that the material located within the mixing chamber 100 are adequately mixed and provides an impedance within the mixing chamber 100 to aid in forming a material spray. Those skilled in the art will appreciate that the position and size of the spray regulator, in cooperation with the size of the spray aperture 94, effects the emitted spray volume.

The present invention further comprises a method of using the present invention to apply a multiple component fluid to a work surface located within the body of a patient The illustrated embodiment comprises a method of practicing the present invention using syringe-type material applicator 34, although those skilled in the art will appreciate that the present invention may effectively couple to a plurality of other applicators.

To use the present invention, the user attaches a spray tip 15 to the elongated body 14 by sliding the outer sleeve 84 of the elongated body 14 towards the interface member 12, thereby exposing the spray tip receiver 90. Thereafter, the user attaches the spray tip 15 to the elongated body 14, wherein the at least one mounting member 96 of the spray tip 15 engages the exposed spray tip receiver 90 on the elongated body 14. The outer sleeve 84 is then slid towards the spray tip 15, thereby locking the spray tip 15 in place. The user may then insert the dispensing tips 48, 60 of the syringe-type material applicator 34 into the receiving apertures 20A, 20B formed on the coupling members 18A, 18B of the interface member 12. Thereafter, the coupling members 18A, 18B are actuated to engage and retain the dispensing tips 48, 60. Typically, syringe-type material applicators 34 are single-use disposable devices constructed of inexpensive plastics and polymers. The application of force to the first piston rod 52 and second piston rod 64 of the syringe-type material applicator 34 will result in the application of the fluid components.

The spray tip 15 may then be inserted into the patient's body and advanced to the area of interest. Once suitably positioned the user applies force to the first piston rod 52 and second piston rod 64 of the syringe-type material applicator 34. Material stored within the syringe reservoirs 42, 54 is advanced through the dispensing tips 48, 60 and into the transport lumens 28A, 28B. The continued application of force advances the material into the elongated body lumens 32A, 32B, which are in communication with the spray tip 15. Thereafter, the material encounters the flexible mixing member 102 positioned within the mixing chamber 100 of the spray tip 15. The mixing member 102 forces the individual materials together and forms a turbulent flow within the mixing chamber 100. The continued application of force expels the mixed material as a spray mixture through the spray aperture 94. Those skilled in the art will appreciate that the present invention permits the user to easily detach and apply the spray tip 15 to the elongated body 14, thereby permitting the user to easily replace the spray tip 15 should the device foul or clog.

In closing it is understood that the embodiments of the invention disclosed herein are illustrative of the principles of the invention. Other modifications may be employed which are within the scope of the invention; thus, by way of example but not of limitation, alternative coupling devices, alternative spray tips, and alternative material applicator devices. Accordingly, the present invention is not limited to that precisely as shown and described in the present invention.

What is claimed is:

1. A laparoscopic spray device useful in applying multiple component materials to locations in vivo, comprising:
    an interface member capable of detachably coupling to a material applicator having at least two material reservoirs storing at least two material components;
    an elongated body having a first end and a second end, said elongated body having at least two lumens therein, said at least two lumens having a first lumen end in fluid communication with said interface member at said first elongated body end and a second lumen end;
    a spray tip having a spray tip proximal end and a spray tip distal end, said spray tip detachably coupled to said second elongated body end at said spray tip proximal end, said spray tip comprising:
        a mixing chamber in communication with said at least two lumens at said second lumen end;
        a spray aperture at said spray tip distal end; and
        a spray forming member positioned within said mixing chamber proximate to said spray aperture; and
    at least one flexible mixing member positioned within said mixing chamber proximate to said second lumen end, said flexible mixing member is configured to flex in response to a force applied by advancing component materials so as to form a narrowing element, and said flexible mixing member is capable of causing impingement mixing of the component materials by forming a turbulent flow within said mixing chamber.

2. The device of claim 1 wherein said interface member further comprises:
    at least two coupling members, said at least two coupling members having at least two receiving apertures formed therein;
    at least two transport lumens disposed within said interface member, said at least two transport lumens in fluid communication with said at least two lumens within said elongated body; and
    said at least two receiving apertures capable of coupling to said at least two material reservoirs.

3. The device of claim 2 wherein said at least two coupling members comprise at least one locking member positioned within each of said receiving apertures, said locking members capable of engaging and retaining said material applicator therein in a snap-fit relation.

4. The device of claim 2 wherein said at least two coupling members comprise:
    at least two outer sleeves having threaded inner walls, said at least two outer sleeve having an inner diameter D; and
    at least two collets defining said receiving apertures, said at least two collets having outwardly threaded bases capable of engaging said threaded inner walls of said at least two outer sleeves, said at least two collets having an outer diameter of D', wherein D' is larger than D.

5. The device of claim 1 wherein said elongated body further comprises:
    a stationary inner body member having said at least two lumens formed therein; and
    a longitudinally slide-able outer body member.

6. The device of claim 5 wherein said elongated body comprises a spray tip receiver disposed on second end, wherein said spray tip receiver capable of engaging and retaining said spray tip.

7. The device of claim 1 wherein said at least two lumens within said elongated body are D-shaped.

8. The device of claim 1 wherein said at least one flexible mixing member comprises a resilient disc having an aperture formed therein.

9. The device of claim 1 wherein said at least one flexible mixing member comprises a flexible washer.

10. The device of claim 1 wherein said elongated body has an elongated body member centrally disposed therein and said at least one flexible mixing member has a resilient nature and is configured to engage said elongated body member and restrict access to said at least two lumens to prevent a backflow of material from said mixing chamber into said at least two lumens.

11. The device of claim 1 wherein said spray tip is detachably coupled to said elongated body in snap-fit relation.

12. A laparoscopic spray device useful in applying multiple component materials to locations in vivo, comprising:
    an interface member capable of detachably coupling to a material applicator having at least two material reservoirs storing at least two material components;
    an elongated body having a first end and a second end, said elongated body having an elongated body member centrally disposed therein and at least two lumens therein, said at least two lumens having a first lumen end in fluid communication with said interface member at said first elongated body end and a second lumen end;
    a spray tip having a spray tip proximal end and a spray tip distal end, said spray tip detachably coupled to said second elongated body end at said spray tip proximal end, said spray tip comprising:
        a mixing chamber in communication with said at least two lumens at said second lumen end;
        a spray aperture at said spray tip distal end; and
        a spray forming member positioned within said mixing chamber proximate to said spray aperture; and
    at least one flexible mixing member positioned within said mixing chamber proximate to said second lumen end, said flexible mixing member has a resilient nature and is configured to engage said elongated body member and restrict access to said at least two lumens to prevent a backflow of material from said mixing chamber into said at least two lumens.

13. The device of claim 12 wherein said interface member further comprises:

at least two coupling members, said at least two coupling members having at least two receiving apertures formed therein;

at least two transport lumens disposed within said interface member, said at least two transport lumens in fluid communication with said at least two lumens within said elongated body; and said at least two receiving apertures capable of coupling to said at least two material reservoirs.

14. The device of claim 13 wherein said at least two coupling member comprise at least one locking member positioned within each of said receiving apertures, said locking members capable of engaging and retaining said material applicator therein in a snap-fit relation.

15. The device of claim 13 wherein said at least two coupling members comprise:

at least two outer sleeves having threaded inner walls, said at least two outer sleeve having an inner diameter D; and at least two collets defining said receiving apertures, said at least two collets having outwardly threaded bases capable of engaging said threaded inner walls of said at least two outer sleeves, said at least two collets having an outer diameter of D', wherein D' is larger than D.

16. The device of claim 12 wherein said elongated body further comprises:

a stationary inner body member having said at least two lumens formed therein; and a longitudinally slide-able outer body member.

17. The device of claim 16 wherein said elongated body comprises a spray tip receiver disposed on second end, wherein said spray tip receiver capable of engaging and retaining said spray tip.

18. The device of claim 12 wherein said flexible mixing member is configured to flex in response to a force applied by advancing component materials so as to form a narrowing element, and said flexible mixing member is capable of causing impingement mixing of the component materials by forming a turbulent flow within said mixing chamber.

19. The device of claim 12 wherein said at least two lumens within said elongated body are D-shaped.

20. The device of claim 12 wherein said at least one flexible mixing member comprises a resilient disc having an aperture formed therein.

21. The device of claim 12 wherein said at least one flexible mixing member comprises a flexible washer.

22. The device of claim 12 wherein said spray tip is detachably coupled to said elongated body in snap-fit relation.

23. A laparoscopic spray device useful in applying multiple component materials to locations in vivo, comprising:

an interface member capable of detachably coupling to a material applicator having at least two material reservoirs storing at least two material components;

an elongated body having a first end and a second end, said elongated body having at least two lumens therein, said at least two lumens having a first lumen end in fluid communication with said interface member at said first elongated body end and a second lumen end;

a spray tip having a spray tip proximal end and a spray tip distal end, said spray tip detachably coupled to said second elongated body end at said spray tip proximal end, said spray tip comprising:

a mixing chamber in communication with said at least two lumens at said second lumen end;

a spray aperture at said spray tip distal end; and a spray forming member positioned within said mixing chamber proximate to said spray aperture; and at least one flexible mixing member positioned within said mixing chamber proximate to said second lumen end, said flexible mixing member is configured to flex in response to a force applied by advancing component materials so as to form a narrowing element, and said flexible mixing member is capable of causing impingement mixing of the component materials by forming a turbulent flow within said mixing chamber; and said flexible mixing member has a resilient nature and is further configured to engage said elongated body member and restrict access to said at least two lumens to prevent a backflow of material from said mixing chamber into said at least two lumens.

* * * * *